US00PP17035P2

(12) United States Plant Patent
Tellwright

(10) Patent No.: US PP17,035 P2
(45) Date of Patent: Aug. 22, 2006

(54) ***NEMESIA* PLANT NAMED 'FLEURAME'**

(50) Latin Name: *Nemesia×hybrida*
Varietal Denomination: Fleurame

(76) Inventor: Martine Tellwright, Highground House, Highground Lane, Barnham, W Sussex (GB), PO22 0BU ( * ) Notice: Subject to any disclaimer, the term of this patent is extended or adjusted under 35 U.S.C. 154(b) by 55 days.

(21) Appl. No.: 11/095,139

(22) Filed: Mar. 30, 2005

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Louanne Krawczewicz Myers

(57) ABSTRACT

A new and distinct cultivar of *Nemesia* plant named 'Fleurame' that is characterized by upright, compact habit, dark-green leaves, and strongly fragrant flowers that are pale pink, lavender and purple in color with yellow eyes and white throats. In combination these characteristics set 'Fleurame' apart from all other existing varieties of *Nemesia* known to the inventor.

2 Drawing Sheets

Genus: *Nemesia.*
Species: *×hybrida.*
Denomination: Fleurame.

BACKGROUND OF THE INVENTION

The present invention relates to a new and distinct cultivar of *Nemesia* plant that is grown as an ornamental for border, patio container or hanging basket. The new cultivar is known botanically as *Nemesia×hybrida* and will be referred to hereinafter by the cultivar name 'Fleurame'. The new variety 'Fleurame' is floriferous, sets few seeds, exhibits upright compact habit, medium-green leaves, and strongly fragrant flowers that appear as shades of soft pink, lavender and purple colors with yellow eyes and white throats.

'Fleurame' is a hybrid that resulted from a formal breeding program begun by the inventor in 1998 at her nursery in West Sussex, United Kingdom. The purpose of the breeding program is to produce new varieties of *Nemesia* that exhibit compact habit, new flower color and improved flower size.

In 2001, the inventor cross-pollinated *Nemesia* seedling #42 (female parent), an unpatented and unreleased selection from a prior cross between the inventor's variety *Nemesia* 'Melanie' (unpatented) and another unnamed seedling from the same program, with *Nemesia* 'Claudette' (male parent), an unpatented selection from the same breeding program. The inventor collected the seed, then sowed and grew to flowering stage many plants from this cross-pollination. The inventor selected 'Fleurame' as a single plant with the desired characteristics described herein.

In comparison with its parents, 'Fleurame' exhibits different flower colors, as follows: the female parent, *Nemesia* seedling #42, carries pink or lilac colored flowers; and the male parent, *Nemesia* 'Claudette', carries darker mauve pink flowers. *Nemesia* seedling #42 is also shorter in height than 'Fleurame', 'Fleurame' was first asexually propagated by the inventor in 2002 in a cultivated area of West Sussex, United Kingdom using softwood cuttings. The distinguishing characteristics of 'Fleurame' have been determined stable and are reproduced true to type in successive generations.

SUMMARY OF THE INVENTION

The following traits have been repeatedly observed and represent the distinguishing characteristics of 'Fleurame'. In combination these traits set the new cultivar apart from all other existing varieties of *Nemesia* known to the inventor. 'Fleurame' has not been tested under all possible conditions and phenotypic differences may be observed with variations in environmental, climatic, and cultural conditions, however, without any variance in genotype.

1. *Nemesia×hybrida* 'Fleurame' exhibits upright, compact habit.
2. The flowers of *Nemesia×hybrida* 'Fleurame' are soft pink, lavender and purple in color with a yellow eyes and white throats.
3. *Nemesia×hybrida* 'Fleurame' exhibits strongly fragrant flowers.
4. *Nemesia×hybrida* 'Fleurame' is an ornamental plant that is suitable for use in borders, patio containers, or hanging baskets.
5. *Nemesia×hybrida* 'Fleurame' achieves 13 cm. in height and 15 cm. in width when grown to flowering in a 1-liter container.
6. *Nemesia×hybrida* 'Fleurame' is asexually propagated using the method of softwood cuttings.
7. *Nemesia×hybrida* 'Fleurame' exhibits dark-green leaves.
8. *Nemesia×hybrida* 'Fleurame' is hardy to minus 6° Centigrade.

BRIEF DESCRIPTION OF THE DRAWINGS

The accompanying color drawings labeled as FIG. 1 and FIG. 2 illustrate the overall appearance of the new *Nemesia* cultivar 'Fleurame' showing the colors as true as it is reasonably possible to obtain in colored reproductions of this type. Colors in the drawings may differ from the color values cited in the detailed botanical description, which accurately describe the actual colors of the new variety 'Fleurame'. The drawings are made from 4-month-old plants grown in 1-liter containers under greenhouse conditions in Encinitas, Calif.

The drawing labeled as FIG. 1 depicts an individual whole plant growing in a 1-liter container.

Figure 1:
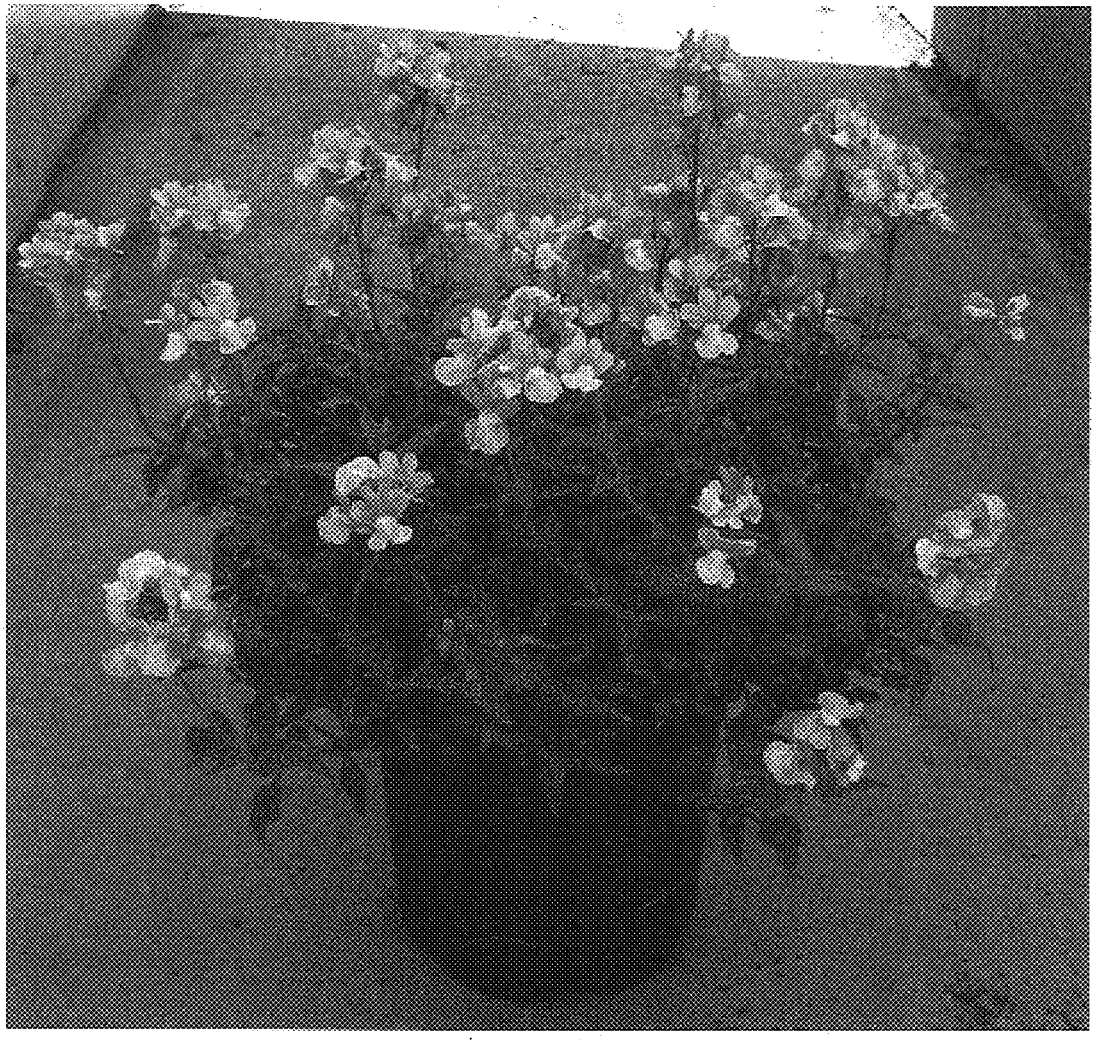
Figure 2:
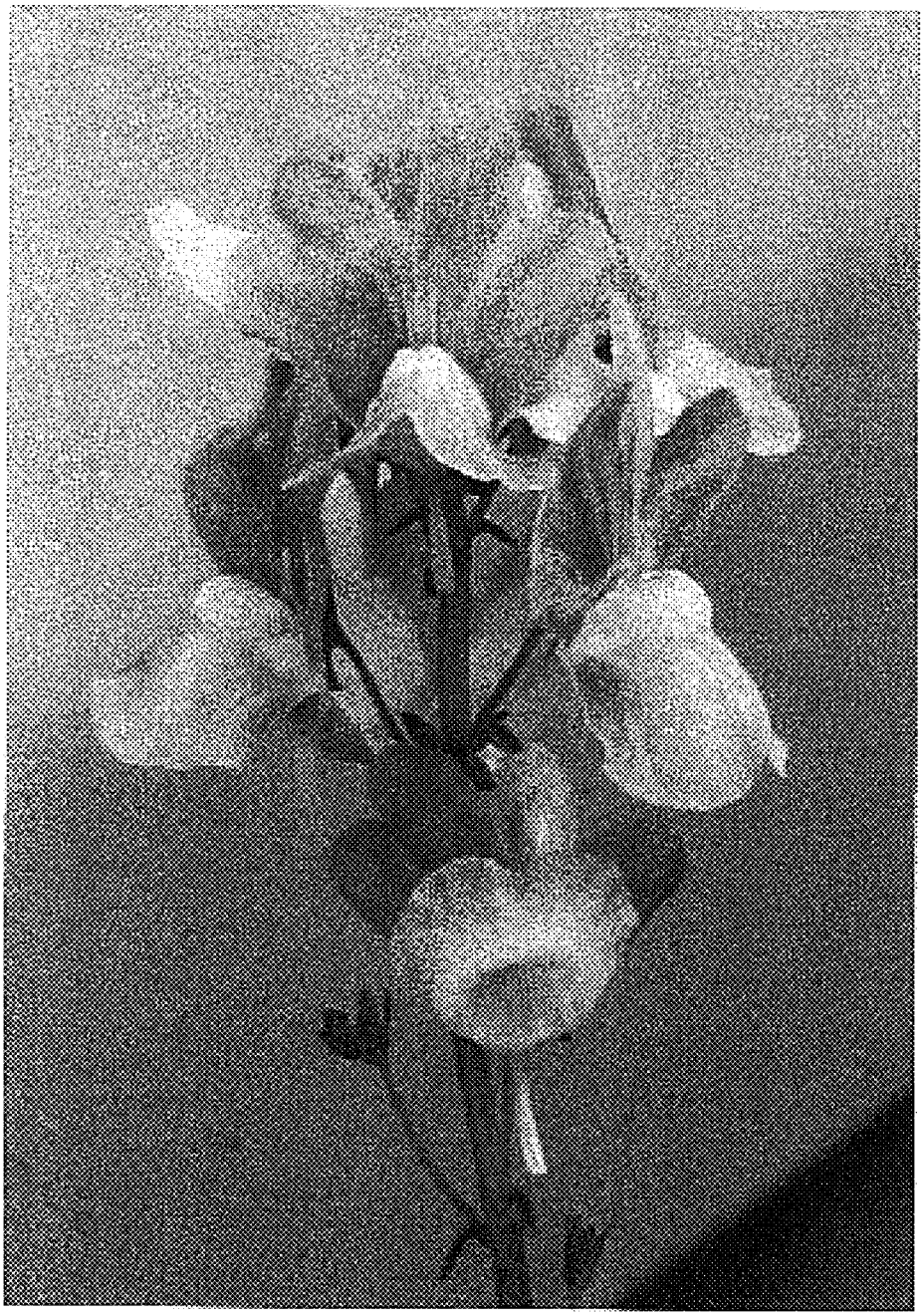

The drawing labeled as FIG. 2 is a close-up view of the flower.

Drawings were made using conventional techniques and although colors may appear different from actual colors due to light reflectance, they are as accurate as possible by conventional photography.

BOTANICAL DESCRIPTION OF THE PLANT

The following is a detailed description of the *Nemesia* plant named 'Fleurame'. Data was collected in 2004 in Arroyo Grande, Calif. from a 3-month old plant grown in 1-liter container under greenhouse conditions. Phenotypic differences may be observed with variations in environmental, climatic, and cultural conditions. The color determinations are in accordance with the 2001 Edition of The Royal Horticultural Society Colour Chart, except where general color terms of ordinary dictionary significance are used.

Botanical classification: *Nemesia×hybrida* 'Fleurame'.
Genus: *Nemesia.*
Species: *×hybrida.*
Denomination: 'Fleurame'.
Commercial classification: Ornamental.
Common name: *Nemesia.*
Suggested uses: For use in borders, patio containers, or hanging baskets.
Suggested commercial container size: 9 cm. or 1-liter commercial containers.
Cultural needs: Full sun, moist acidic well-draining soil and regular water.
Parentage: *Nemesia* 'Fleurame' is a hybrid that resulted from the cross-pollination of the following parent plants:
*Seed parent.*—*Nemesia* seedling #42.
*Pollen parent.*—*Nemesia* 'Claudette'.
Propagation: Softwood cuttings.
Growth habit: Upright, compact habit.
Vigor: Vigorous.
Plant dimensions: 13 cm. in height and 15 cm. in width when grown to flowering in a 1-liter container.
Type: Perennial.
Seasonal interest: Blooms in spring with flowers that are purple in color with yellow eyes and white throats.
Time to initiate roots: Approximately 14 days are needed to develop roots on initial cuttings.
Temperatures to initiate rooting: The air temperature that is recommended for rooting is 16° Centigrade and the soil temperature that is recommended for rooting is 24° Centigrade.
Crop time: Approximately 8 weeks are needed to produce a finished 9 cm. container plant from a rooted cutting, and 2–3 months are needed to produce a finished 1-liter container plant from a rooted cutting.
Root system: Fine.
Hardiness: Hardy to minus 6° Centigrade.
Disease and pest susceptibility: 'Fleurame' is susceptible to viruses and whitefly.
Special growing requirements:
*Pruning.*—Pinch back when potted from plug to commercial container.
*Soil.*—70% medium grade peat, 10% coarse peat and 20% 12 mm. bark.
*Light.*—Normal daylight.
Growing problems: None known to the inventor.
Stem:
*Stem shape.*—Quadrate.
*Stem length.*—20 cm. in length.
*Stem diameter.*—3 mm. in diameter.
*Stem surface.*—Glabrous.
*Stem color.*—137D.
*Pubescence.*—None observed.
*Stem texture.*—Flexible and fleshy.
*Internode length.*—1.50 cm. between nodes.
*Branching habit.*—Ascending.
Foliage:
*Leaf arrangement.*—Opposite.
*Type.*—Evergreen.
*Leaf shape.*—Oval.
*Leaf division.*—Simple.
*Apex.*—Acute.
*Base.*—Rounded.
*Margins.*—Dentate.
*Surface.*—Glabrous.
*Leaf pubescence.*—None observed.
*Leaf length.*—Individual leaves range from 2–3 cm. in length.
*Leaf width.*—Individual leaves range from 0.75–1.50 cm. in width.
*Leaf color* (*adaxial surface*).—137A.
*Leaf color* (*abaxial surface*).—N138B.
*Leaf attachment.*—Petiolate.
*Petiole shape.*—Sulcate.
*Petiole surface.*—Glabrous.
*Petiole dimensions.*—6 mm. in length and 1.75 mm. in diameter.
*Petiole color.*—137A.
*Vein pattern.*—Pinnate.
*Vein color* (*adaxial surfaces*).—137A.
*Vein color* (*abaxial surfaces*).—N138B.
Flowers:
*Flowering season.*—Spring.
*Fragrance.*—Strongly perfumed scent.
*Self-cleaning or persistent.*—Self-cleaning.
*Type of inflorescence.*—Corymb.
*Quantity of flowers.*—An average of 25 flowers per 1-liter container plant.
*Inflorescence dimensions.*—4 cm. in length and 4 cm. in width.
*Peduncle dimensions.*—3 cm. in length and 2 mm. in diameter.
*Peduncle shape.*—Quadrate.
*Peduncle surface.*—Glabrous.
*Peduncle color.*—139B.
*Pedicel dimensions.*—9 mm. in length and 0.25 mm. in diameter.
*Pedicel shape.*—Quadrate.
*Pedicel surface.*—Glabrous.
*Pedicel color.*—139C.
*Bud shape.*—Cordate.
*Bud color.*—64B.
*Bud surface.*—Glabrous.
*Bud dimensions.*—7 mm. in diameter and 7 mm. in length.
*Quantity of buds.*—An average of 25 individual buds per 1-liter container plant.
*Flower shape.*—Personate.

*Flower dimensions.*—2 cm. in length and 2 cm. in width.
*Flower color* (*adaxial and abaxial surfaces*).—Individual colors 5A, 75A, 155A, and 76A are present on an individual flower.
*Corolla tube dimensions.*—6 mm. in length and 2 mm. in diameter.
*Corolla tube color* (*inner and outer surfaces*).—155A.
*Palate color* (*eye of flower*).—Adaxial surface is 5A and abaxial surface is 5D.
*Palate dimensions.*—3 mm. in length and 5 mm. in width.
*Nectary color.*—3A.
*Nectary dimensions.*—3 mm. in width and 6 mm. in length.
*Nectary surface.*—Lanate.
*Upper lip dimensions.*—2 cm. in width and 1 cm. in length.
*Upper lip color* (*adaxial and abaxial surfaces*).—Individual colors 76A and 75A are individually present.
*Lower lip dimensions.*—2 cm. in width and 1 cm. in length.
*Lower lip color* (*adaxial and abaxial surfaces*).—Individual colors 76A, 5A, and 75A are individually present.
*Upper lip margins.*—Lobed and entire.
*Lower lip margin.*—Entire.
*Number of lobes* (*upper lip*).—Four lobes in number.
*Fused or unfused* (*upper lip*).—Lobes basally fused.
*Lobe dimensions* (*upper lip*).—Each lobe is 5 mm. in width and 6 mm. in length.
*Upper lip apices.*—Each lobe exhibits a rounded apex.
*Lower lip apex.*—Closest to emarginate.
*Upper lip surfaces* (*adaxial and abaxial*).—Glabrous.
*Lower lip surfaces* (*adaxial and abaxial*).—Glabrous.
*Calyx dimensions.*—3 mm. in length and 4 mm. in width.
*Calyx shape.*—Explanate.
*Sepals.*—Five in number.
*Sepal dimensions.*—2 mm. in length and 1 mm. in width.
*Sepal surface.*—Glabrous.
*Sepal shape.*—Lanceolate.
*Sepal apex.*—Acute.
*Sepal base.*—Cuneate.
*Sepal margin.*—Entire.
*Sepals fused or unfused.*—Unfused.
*Sepal color* (*adaxial surface*).—137B.
*Sepal color* (*abaxial surface*).—137B.
*Lastingness of individual flower on the plant.*—An individual flower lasts 7–10 days.

Reproductive organs:
*Stamens.*—Two in number.
*Color of stamens.*—155A.
*Stamen dimensions.*—2 mm. in length and less than 0.25 mm. in diameter.
*Anther color.*—5C.
*Amount of pollen.*—Moderate.
*Pollen color.*—5C.
*Anther dimensions.*—1 mm. in length and less than 0.50 mm. in width.
*Pistil.*—One.
*Pistil color.*—144D.
*Pistil dimensions.*—1 mm. in length and 0.25 mm. in diameter.
*Ovary dimensions.*—Less than 0.50 mm. in height and less than 0.50 mm. in diameter.
*Ovary shape.*—Globular.
*Ovary position.*—Superior.
*Ovary color.*—144D.

Seed:
*Quantity of seed.*—On average, approximately 2 per flower.
*Seed shape.*—Flattened oval.
*Seed color.*—200D.
*Seed dimensions.*—An average of 2 mm. in length and 1.25 mm. in width.

What is claimed is:

1. A new and distinct cultivar of *Nemesia* plant named 'Fleurame' as described and illustrated herein.

* * * * *